United States Patent [19]

Brånemark

[11] Patent Number: 5,041,139

[45] Date of Patent: Aug. 20, 1991

[54] ANCHORING ELEMENT FOR SUPPORTING A JOINT MECHANISM OF AN ANKLE, HIP OR OTHER RECONSTRUCTED JOINT

[76] Inventor: Per-Ingvar Brånemark, Andergatan 3, S-431 39 Mölndal, Sweden

[21] Appl. No.: 406,587

[22] Filed: Sep. 13, 1989

[30] Foreign Application Priority Data

Apr. 25, 1989 [SE] Sweden .................. 8901509

[51] Int. Cl.$^5$ ..................., A61F 2/42; A61F 2/32
[52] U.S. Cl. ........................ 623/21; 623/22; 623/18
[58] Field of Search ............... 123/16, 18, 19, 20, 123/21, 22

[56] References Cited

U.S. PATENT DOCUMENTS

| | | | |
|---|---|---|---|
| 3,893,196 | 7/1975 | Hochman | 623/23 X |
| 4,790,852 | 12/1988 | Noiles | 623/16 |
| 4,790,852 | 12/1988 | Noiles | 623/16 |
| 4,838,891 | 6/1989 | Branemark et al. | 623/20 |
| 4,908,032 | 3/1990 | Keller | 623/23 X |
| 4,936,856 | 6/1990 | Keller | 623/22 |
| 4,944,759 | 7/1990 | Mallory et al. | 623/22 |

FOREIGN PATENT DOCUMENTS

| | | | |
|---|---|---|---|
| 0098224 | 1/1984 | European Pat. Off. | 623/23 |
| 2627380 | 8/1989 | France | 623/18 |
| 2137098 | 10/1984 | United Kingdom | 623/23 |
| 8503425 | 8/1985 | World Int. Prop. O. | 623/20 |
| 8503426 | 8/1985 | World Int. Prop. O. | 623/22 |
| 8603962 | 7/1986 | World Int. Prop. O. | 623/23 |
| 8909579 | 10/1989 | World Int. Prop. O. | 623/20 |

Primary Examiner—David J. Isabella
Assistant Examiner—David H. Willse

[57] ABSTRACT

An anchoring element for supporting a joint mechanism of a reconstructed joint is discussed. The anchoring element includes an at least partially hollow guide and centering sleeve for supporting the joint mechanism. The anchoring element is compatible with bone and marrow tissue and has a surface which can be at least partially osseo-integrated with the tissue to achieve permanent anchorage in the bone and marrow tissue. The anchoring element can be used to reconstruct an ankle joint or a hip joint.

8 Claims, 3 Drawing Sheets

ANCHORING ELEMENT FOR SUPPORTING A JOINT MECHANISM OF AN ANKLE, HIP OR OTHER RECONSTRUCTED JOINT

BACKGROUND OF THE INVENTION

1. Field of the Invention

The present invention relates to an anchoring element for supporting a joint mechanism of a reconstructed joint, a method of reconstructing an ankle or hip joint, and a reconstructed joint.

The preferred embodiments of the invention will be described in the following with reference to the reconstruction of ankle and hip joints. However, the invention is not limited thereto. The invention can be used for other similar joints, particularly load-carrying joints. The invention can also be used in reconstructions after amputation or other defects.

2. Description of the Related Art

For some considerable time, attempts have been made to replace damaged joints by artificial prostheses. These have been anchored in the bone tissue, either directly or via an intermediate adhesive layer, usually bone cement. Various materials have been used for the prostheses, such as stainless steel, chrome and cobalt alloys, titanium alloys, aluminum alloys, ceramic material, carbon fiber, and many other materials. Great inventiveness has been exhibited in the surfaces and surface properties proposed for obtaining the best possible anchoring stability.

The greatest problem in orthopedic prosthesis surgery is still how best to secure the components of the prostheses to the patient's bone tissue. Experiments entailing mechanical locking between implant and bone tissue (press-fit, see for instance EP 149 527), and the use of bone cement (polymethylmethacrylate) have not been sufficiently successful.

Conventionally, prostheses are secured within bones with cement. Great care is taken to remove the marrow from the exposed bone—the cavity is even flushed clean—before the prosthesis is inserted and then secured to the, bone with cement. However, cemented prostheses often loosen. This is particularly the case with prostheses cemented within load-carrying joints, such as ankle and hip joints. It has also been found that, if used before hardening, bone cement tends to seep out into the adjacent bone tissue. Initially, this offers a certain mechanical stability but with young, overweight or more active individuals, the joint between bone and cement is finally destroyed, resulting in micro-movement. A layer of connective tissue grows between prosthesis and bone, and the joint finally loosens.

The other method used today is the "cementless" method which aims at biologically securing the prosthesis, i.e., direct contact is desired between prosthesis and bone tissue with no intermediate layer of connective tissue or adhesive. To achieve satisfactory anchoring stability, various materials and surface structures for the prosthesis have been tested and a technique known as "press-fit" has been used to retain the prosthesis in position after insertion. However, recently published experiments (see Schimmel et Huiskes, "Primary fit of the Lord cementless total hip", Acta. Orthop. Scand. 1988: 59(6): 638–642) indicate that this method does not function in reality. It has been shown that extremely unfavorable threepoint loading with stress concentrations is obtained (EP 176 711).

The problem cannot be solved merely by selecting the "correct surface or material". There are a number of other factors of decisive significance.

Attempts have therefore been made in recent years to use titanium fixtures anchored in the marrow cavity of the bone to become osseo-integrated, as described by Hagert et al. "Metacarpophalangal Joint Replacement with Osseo-integrated Endoprostheses" in Scand. J. Plast. Reconstr. Surg. 20: pages 207–218, 1986.

It is known to permanently anchor oral and extra-oral prostheses in bone tissue. This osseo-integration technique for dentistry has been developed over the last 25 years by Professor Branemark and his colleagues, with excellent results in applying fixtures in the jawbone to hold teeth or arch attachments. However, the experiments performed by Hagert to apply this technique to the reconstruction of finger joints have not fulfilled expectations. The unacceptable results are evidently due to the entirely different conditions encountered when using this "dental technique" in the prosthetic reconstruction of fingerjoints. These problems are of course increased in the case of ankle and hip joint prostheses since totally different loads are placed on these joints.

Today, the main problem in orthopedic prosthesis surgery is still loosening of the bone anchoring unit. However, with a success rate for dental implants of more than 90% over a 20 year period, a number of other problems arise which, so far, have been unnecessary to take into account. One of the major problems is increased wear on the joint mechanism. A different type of prosthesis design from that used hitherto is required if the osseo-integration method is to be applied. To enable the joint mechanism to be replaced without disturbing the bone-anchorage, the prosthesis system must be divided into components where the joint mechanism element can be separated from the actual bone-anchoring element. Furthermore, if the two-stage method is used, it must be possible to connect the joint mechanism in the second stage if the patient, or at least the patient's reconstructed joint, is not to be kept immobilized. Two factors must therefore be taken into account: First, the joint mechanism is subject to wear and therefore must be replaceable. Second, to use the two stage method, the joint mechanism must be replaceable.

SUMMARY OF THE INVENTION

It has now surprisingly been found that the problems and drawbacks of the techniques described above can be eliminated by the present invention.

The invention is directed to an anchoring element for supporting a joint mechanism of a reconstructed joint, the anchoring element including an at least partially hollow guide and centering sleeve for supporting the joint mechanism, the anchoring element being formed of material which is compatible with bone and marrow tissue, the anchoring element having a surface which can be at least partially osseo-integrated with the tissue to achieve permanent anchorage in the bone and marrow tissue.

The invention is also directed to a reconstructed joint, a method of reconstructing an ankle joint, and a method of reconstructing a hip joint.

Other features and advantages of the invention will become apparent from the following description of preferred embodiments of the invention, with reference to the accompanying drawings.

DESCRIPTION OF THE PREFERRED EMBODIMENTS

Figure 1:
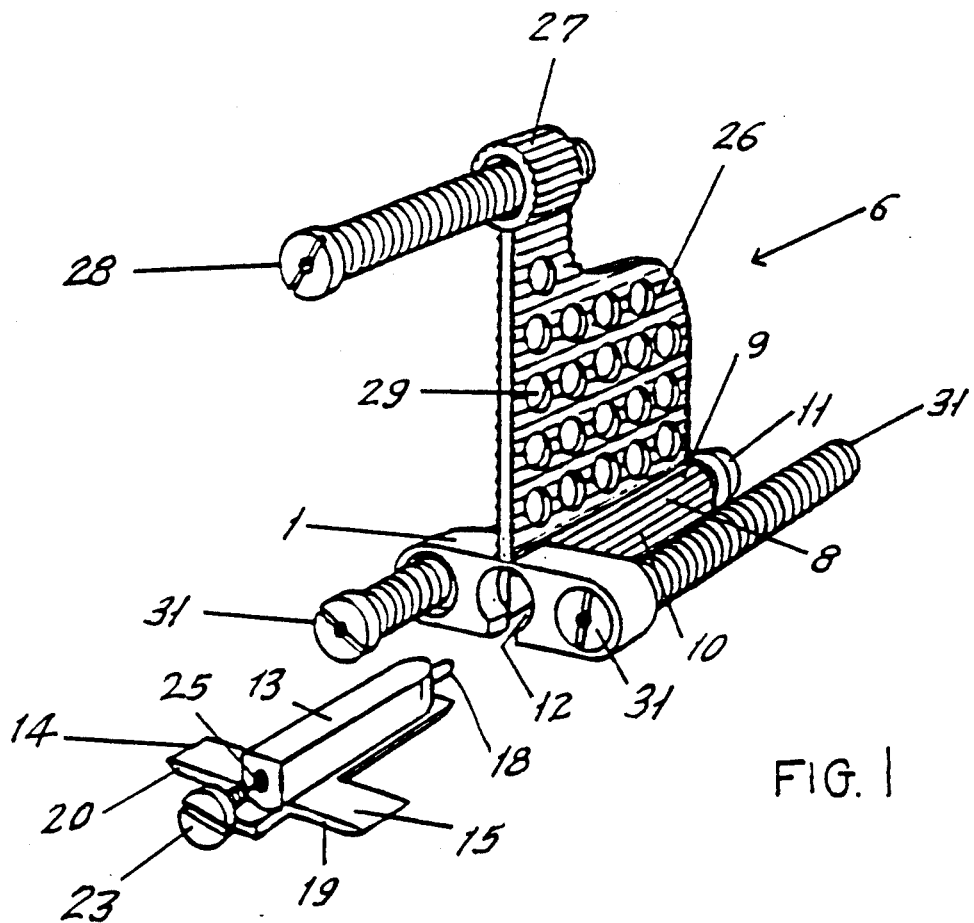
FIG. 1 is an exploded view of an anchoring element in accordance with a first embodiment of the invention.

Referring to FIG. 1, a non-rotationally symmetrical anchoring element 6 in accordance with a first embodiment of the invention includes a front plate 1. A hollow central guide and receiving sleeve 8 protrudes rearwards from the plate 1. The sleeve 8 is substantially cylindrical and is provided with longitudinal corrugations 10 along its radially outer surface. The corrugations 10 promote integration. These corrugations 10 may suitably be identical to an axial section of tapped, rotation-symmetrical fixtures used in dentistry. The end 9 of the sleeve 8 facing away from the front plate 1 is internally threaded to match the external threading on a bolt 11.

The side of the sleeve 8 facing the joint is slit, revealing a hollow space 12 for receiving an insert 13 in a first step (described below). The rear of the insert 13 has a dowel 18 which fits into a corresponding recess (not illustrated) in the bolt 11 when the insert 13 is in place. Wings 14, 15 protrude substantially perpendicularly from the front end of the insert 13. When the insert 13 is in place, the wings 14, 15 fit into recessed flat surfaces 16, 17 (FIG. 2) on each side of the slit and hollow space 12. The front edges 19, 20 of the wings 14, 15 are thus brought into contact with shoulders 21, 22 on the front plate 1 when the insert 13 is finally positioned by a screw 23 cooperating with a hole 25 in the front of the insert 13. The insert 13 also has a front extension 24. The front plate 1 has two holes, one on each side of the sleeve 8, for receiving attachment screws 31.

The anchoring element 6 (FIG. 1) includes a central, winglike plate 26 protruding from the sleeve 8. The anchoring element 6' (FIG. 2) does not have such a plate. The upper end of the plate 26, facing away from the sleeve 8, has a guide sleeve 27 for receiving a screw 28. Both the plate 26 and the guide sleeve 27 are provided with longitudinal corrugations which, like the corrugations 10, extend in the direction of insertion of the anchoring element 6. The corrugations promote integration. The plate 26 includes a plurality of holes 29. The holes 29 define cutting edges.

Figure 2:
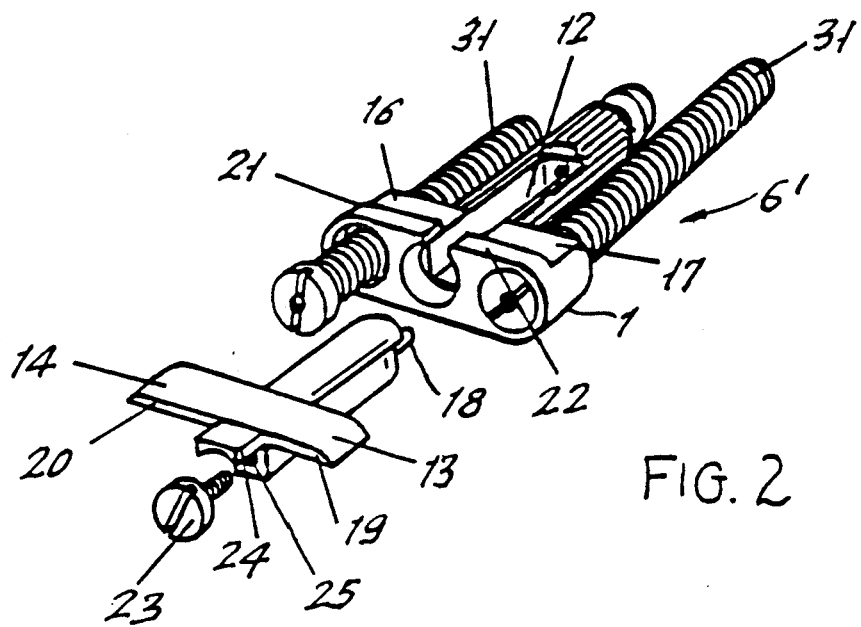
FIG. 2 is an exploded view of an anchoring element in accordance with a second embodiment of the invention. The anchoring element of FIG. 2 generally corresponds to the anchoring element of FIG. 1 except that the anchoring element of FIG. 2 does not have a winglike plate, and is in an inverted position.

The anchoring elements 6, 6' of FIGS. 1 and 2, respectively, are preferably made entirely of titanium. The surfaces of the insert 13 and the front plate 1 are not corrugated, so as not to promote integration. When the anchoring element 6 (or 6') becomes integrated into the bone tissue, the insert 13 will be removed and replaced by a permanent insert 13' (FIG. 4), with an artificial joint mechanism B.

Figure 3:
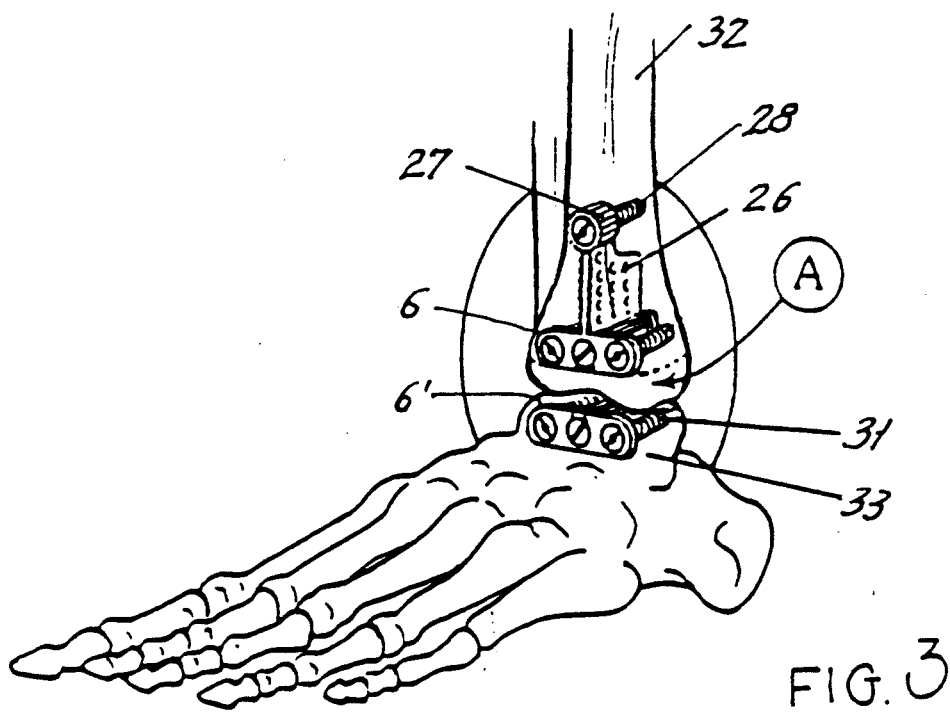
FIG. 3 is a perspective view of the first stage of an ankle reconstruction using the anchoring elements of FIGS. 1 and 2.
Figure 4:
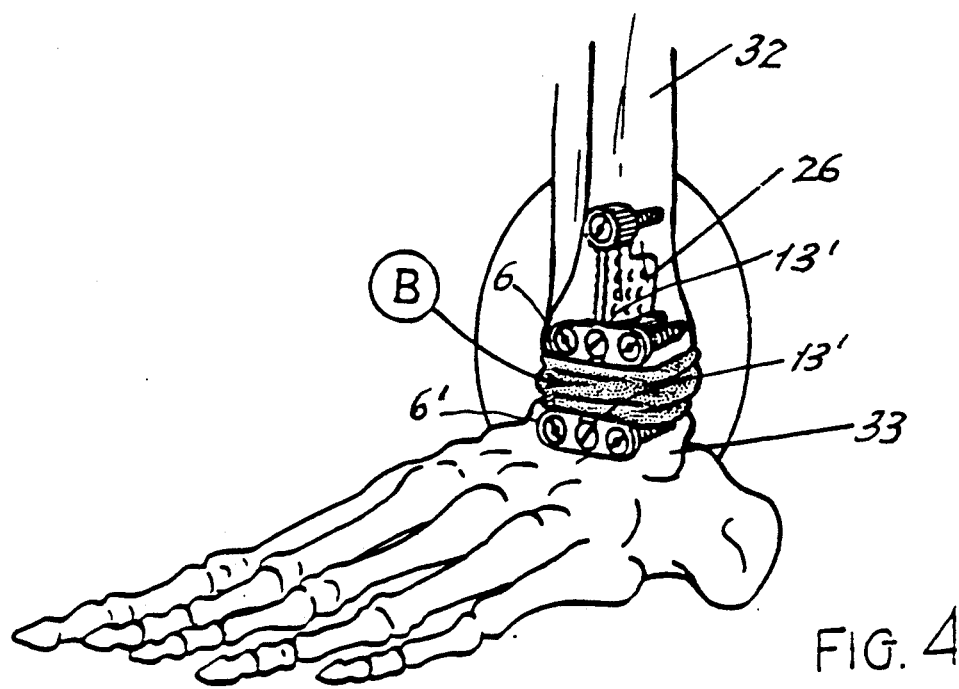
FIG. 4 is a perspective view, similar to FIG. 3, of the finished reconstruction.

Thus, referring to FIG. 3, the invention allows the original joint A to remain intact until the anchoring elements 6, 6' have become integrated. The defective joint A is then replaced by the artificial joint B. The artificial joint B is positioned between the anchoring elements 6, 6', as illustrated in FIG. 4.

In operation, the skin over the tibia 32 (or shin bone) and the talus 33 (or ankle bone) close to the joint A is opened and suitable midpoints are determined for centering the anchoring element 6. Four holes are then carefully drilled in the tibia 32, and three corresponding holes are carefully drilled in the talus 33. The holes in the tibia 32 and the talus 33 are connected together by slots. Accurate preparation is then performed, the anchoring elements 6, 6' constituting the final preparation when screws 31, 28 are screwed in. The recesses in the front plate 1 and in the sleeve 27 serve as guides for the screws 31, 28. The screws 31, 28 provide additional stability and position the anchoring elements 6, 6'. Once the anchoring elements 6 6' have been positioned, a smoothly polished insert 13 is inserted into the sleeve 8 of each anchoring element 6, 6'. The anchoring elements 6, 6' are then left within the bones 32, 33 for osseo-integration to take place. The integration period for anchoring elements inserted in the bone close to a joint for reconstruction of an ankle bone is between 3 and 6 months. The joint A is entirely intact during integration of the two anchoring elements 6, 6'.

After the integration period, the destroyed or damaged joint A is removed and replaced by the artificial joint mechanism B. The artificial joint mechanism B is suitably secured via inserts 13' facing each other in the respective anchoring elements 6, 6'. Alternatively, the artificial joint B may be prepared in advance with two similar inserts 13'. In the latter case, the inserts 13 present in the guide sleeves 8 during the integration period are replaced by the new inserts 13'.

Instead of the two-stage procedure described above, the ankle joint can of course be reconstructed in one step. However, in such a reconstruction, there is the problem of loading the ankle joint before the anchoring elements 6, 6' become sufficiently integrated.

The anchoring elements 6, 6' may be used without the special anchoring screws 31, 28, relying only on the automatic integration of the anchoring elements 6, 6' into the bone tissue. However, in the case of joints which must take a certain load, such as ankle joints, these screws 31, 28 help distribute the load and accurately position the anchoring elements 6, 6'.

In the ankle joint reconstruction illustrated in FIGS. 1-4, the anchoring elements 6, 6' are transverse to the longitudinal axis of the ankle. The two anchoring elements 6, 6' use the same basic principle, but the anchoring element 6 for the tibia 32 has the special stabilizing and anchoring wing or plate 26. There is no space for such a plate in the ankle bone 33. However, even in the tibia 32, the support plate 26 is not imperative. Two anchoring elements 6' (of the type illustrated in FIG. 2) could be used to achieve the necessary joint reconstruction.

The invention, with stable osseo-integration of the anchoring elements 6, 6' in the bone tissue, is based on extensive experimental biological analysis of the structure and function of joints in the course of a disease or in a defective state after wear or inflammatory decomposition of bone tissue, and after extensive study of the vascular supply to bone marrow. It has thus been established that synthetic replacement of destroyed articular cartilage and ligament must be based on the basic principle that bone and marrow tissue constitute a structural and functional unit. Cooperation between the two components, at least considered over a longer period of time, is absolutely necessary if the hard tissue is to function as a support element.

The invention is thus based on the realization that when anchoring a prosthetic replacement for a joint surface and ligament to parts of the skeleton close to a joint, the interaction between bone marrow and bone tissue must be respected. Attachment elements used for this purpose according to the invention are thus made of a material compatible with tissue and are given a surface structure which will ensure biologically correct integration with marrow and bone tissue. In particular, holes 29 in the plate 26 naturally facilitate such integration. When the anchoring element 6 is being inserted, the edges of the holes 29 perform a cutting function and ensure that the base plate fits well into the surrounding tissue, and part of the tissue is directed through the holes 29 to give adequate integration of the anchoring element 6 into its surroundings.

Figure 5:
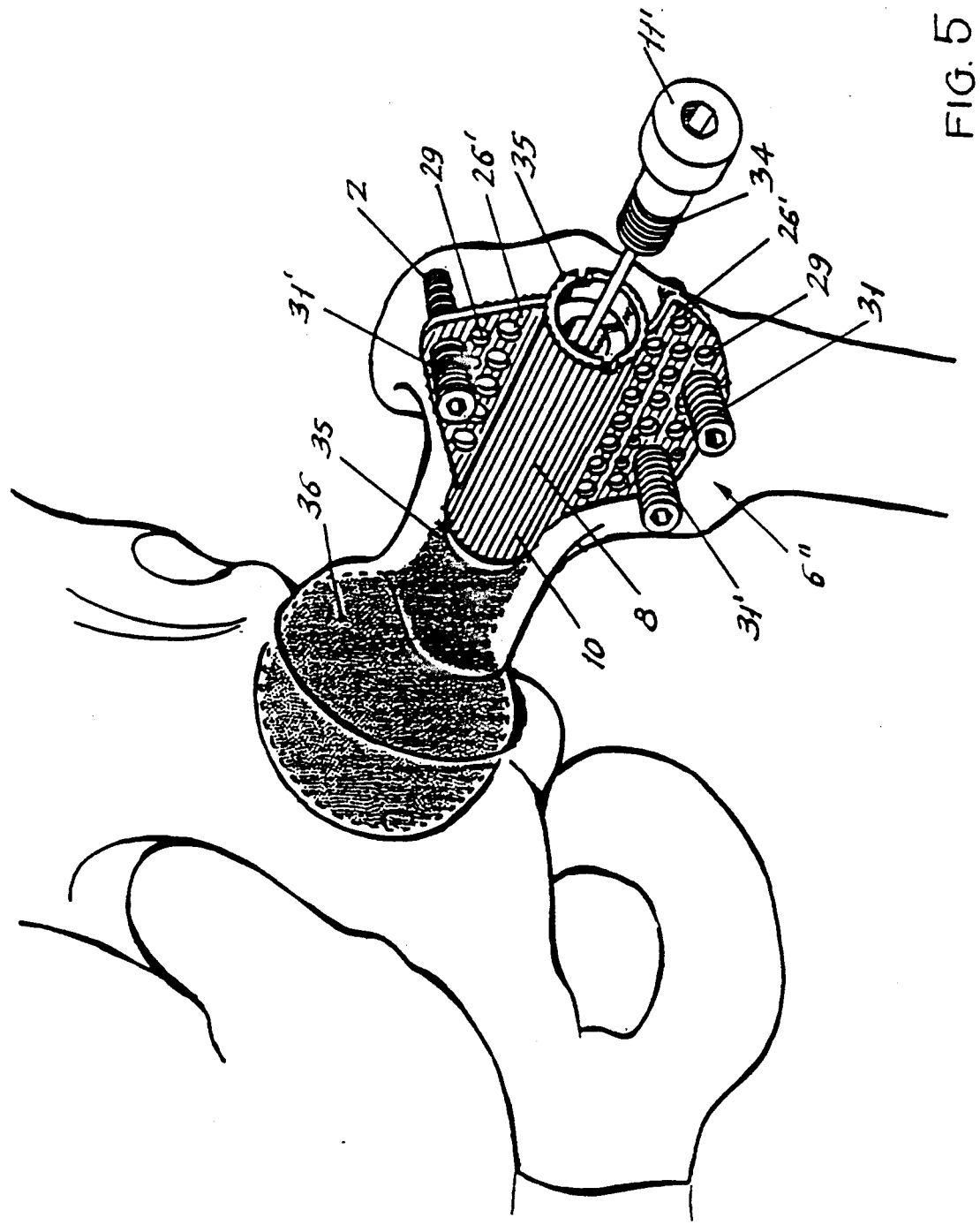
FIG. 5 is a perspective view of a hip joint reconstruction using an anchoring element in accordance with a third embodiment of the invention.

Referring to FIG. 5, which illustrates a reconstructed hip joint, an anchoring element 6" is used which has one central guide sleeve 8 with longitudinal corrugations 10 running in the direction of insertion. Unlike the anchoring element 6, the element 6" is, for reasons of space, provided with two winglike plates 26' protruding from the sleeve 8. As in the previous basic constructions, the plates 26' have through-holes 29 with cutting edges. Through-holes for screws 31' are also provided in the plates 26'. The screws 31' have different diameters so that, when screwed into the holes, they come into contact with the plates 26', thus preventing ends 2 from causing damage in the bone. The plates 26' are also provided with corrugations 10 running in the direction of insertion to facilitate favorable integration of the anchoring element 6" into the bone and marrow tissue. The end of the guide sleeve 8 facing away from the hip joint is closed by a dowel-like screw 11'. Threads 34 are provided on the screw's lower end facing the joint so that the screw 11' can be screwed into the end 35 of the sleeve 8 which receives an artificial joint 36. All parts of the anchoring element 6" are made of titanium.

In operation, a lateral incision is made and a Kirschner wire is inserted through lateral cortices, up into the collum. Simultaneous fluoroscopy enables orientation in two planes. A relatively large hole is then drilled to receive the sleeve 8, and slots are formed to receive the plates 26'. Perpendicular holes are then drilled for the screws 31'. The latter holes have two different diameters to match the diameters of the screws 31'. The joint is then allowed to become integrated. The artificial joint mechanism 36 is finally applied at the conclusion of the integration period. Alternatively, the entire operation may be performed in one step.

When inserted in the tissue, the anchoring elements act as a preparation instrument. Special preparation instruments may alternatively be used to achieve optimum conditions for integration into the bone and may be left there as additional support and to further optimize stability. Integration depends partly on the cutting edges of the anchoring elements which give perfect congruence with the surrounding tissue.

The basic principle of the present invention is thus the discovery that bone and marrow tissue constitute a structural and functional unit and the interaction between them must therefore be respected when undertaking reconstructive surgery. This means that, as far as technically possible, communication must be permitted between marrow and bone tissue.

Although the invention has been described in relation to a preferred embodiment thereof, many other variations and modifications and other uses will become apparent to those skilled in the art. It is preferred, therefore, that the invention be limited not by the specific disclosure herein, but only by the appended claims.

What is claimed is:

1. An anchoring element for supporting a joint mechanism of a reconstructed joint, said anchoring element comprising an at least partially hollow guide and centering sleeve for supporting the joint mechanism, said anchoring element being formed of material which is compatible with bone and marrow tissue, said anchoring element having a surface which can be at least partially osseo-integrated with the tissue to achieve permanent anchorage in the bone and marrow tissue;
   a front plate, said sleeve protruding from said front plate, said sleeve having a slit and a hollow cavity for connecting the joint mechanism to said anchoring element; and
   an insert removably positioned in said sleeve, said insert covering said slit and said hollow cavity.

2. An anchoring element for supporting a joint mechanism of a reconstructed joint, said anchoring element comprising an at least partially hollow guide and centering sleeve for supporting the joint mechanism, said anchoring element being formed of material which is compatible with bone and marrow tissue, said anchoring element having a surface which can be at least partially osseo-integrated with the tissue to achieve permanent anchorage in the bone and marrow tissue; and
   a substantially flat, winglike plate protruding from said sleeve;
   wherein said sleeve has a major axis, said winglike plate having longitudinal corrugations and holes with cutting edges, said longitudinal corrugations being parallel to said major axis.

3. The anchoring element of claim 2, wherein said anchoring element is an anchoring element for supporting a joint mechanism of an ankle joint.

4. The anchoring element of claim 2, wherein said anchoring element is an anchoring element for supporting a joint mechanism of a hip joint.

5. The anchoring element of claim 2, wherein said anchoring element is not rotationally symmetrical.

6. The anchoring element of claim 2, wherein said anchoring element consists entirely of titanium.

7. The anchoring element of claim 2, further comprising an anchoring screw, said winglike plate including a hole for receiving said screw, said screw being located at an end of said winglike plate facing away from said sleeve.

8. The anchoring element of claim 2, further comprising an attachment screw, said screw having two different diameters for positioning said screw with respect to said winglike plate.

* * * * *